United States Patent [19]

Sherva-Parker

[11] Patent Number: 4,743,264
[45] Date of Patent: May 10, 1988

[54] EXTERNAL PROTHESIS WITH MAGNETIC FIELD

[76] Inventor: Carole J. Sherva-Parker, Route 1, Box 152, Thief River Falls, Minn. 56701

[21] Appl. No.: 11,304

[22] Filed: Feb. 5, 1987

[51] Int. Cl.⁴ ............................................. A61F 2/78
[52] U.S. Cl. ........................................ 623/33; 623/16
[58] Field of Search .............................. 623/27, 33-37, 623/16, 18

[56] References Cited

U.S. PATENT DOCUMENTS

| | | | |
|---|---|---|---|
| 2,578,019 | 12/1951 | Ryan | 623/36 |
| 3,889,301 | 6/1975 | Bonner | 623/37 |
| 4,128,903 | 12/1978 | Maush | 623/36 |
| 4,547,912 | 10/1985 | Sherva-Parker | 623/16 |

Primary Examiner—Richard J. Apley
Assistant Examiner—James Prizant
Attorney, Agent, or Firm—Arnold S. Weintraub

[57] ABSTRACT

Disclosed is an external prosthesis with a magnetically transmissive/receptive layer for use with an internal prosthesis attachable to the stump of a residual limb. The external prosthesis comprises a synthetic body member having a concave socket formed at an end thereof. The socket is sized to receive the stump of a residual limb with an internal prosthesis installed. The socket has disposed on its concave external surface a magnetically transmissive/receptive layer. Magnetic attraction between the magnetically transmissive/receptive layer and the magnetically attractive internal prosthesis will ensure a secure and non-slip installation of the external prosthesis on the residual limb of the user. The external prosthesis may further comprise a pressure deformable layer disposed atop, beneath or within the magnetically transmissive/receptive layer, or provide alternating pressure through breaking and re-establishing magnetic attraction as would occur through interrupting an electromagnetic force to its recipient.

13 Claims, 2 Drawing Sheets

EXTERNAL PROTHESIS WITH MAGNETIC FIELD

BACKGROUND OF THE INVENTION

1. Field of the Invention:

This invention relates, in general, to protheses which are externally attachable to severed or amputated limbs and, more specifically, to an external prosthesis attachable to a severed or amputated limb which employs a magnetic field to help provide a secure, non-slip fit.

2. Description of the Prior Art:

It is common to attach a prosthesis or artificial limb externally onto the stump of a limb of an individual which has been amputated or otherwise severed in order to provide a measure of use of the limb to the individual. In general, prior art external prostheses employ a concave socket formed at the attachment end to receive the residual limb. The socket is generally configured to accommodate the residual limb, and generally contains some type of padding material to help cushion the end of the residual limb. The strap and harness assembly is utilized to attach the external prothesis to the stump of the limb. During use of the weight bearing limb, such as a leg or arm, forces are generated which are transmitted through the prothesis directly through the flesh surrounding the stump. Since it is difficult to insure a secure, non-slip engagement between the prothesis and the limb, the forces generated during use of the prosthesis create movement of the prosthesis relative to the stump which results in irritation of the flesh surrounding the stump and discomfort to the wearer. This makes it difficult, if not impossible to effectively use the prosthesis in a normal manner.

Various solutions to the above-listed problems have been proposed. Some, such as U.S. Pat. No. 2,578,019, concern themselves with the external prosthesis itself. Others, such as my U.S. Pat. No. 4,547,912, proposes using an internal prothesis attachable to the external prothesis. My patent proposes employing an amputation apparatus comprising two parts. The first part is a cap having an internal cavity for insertion over the bone and an opposed outwardly extending boss. The second part comprises a plate having an internal cavity mountable over the outwardly extending boss of the cap. The plate has a radial extent substantially greater than the radial extent of the cap to define equally weight distribution surface for internal and external forces over the entire bottom surface of the stump.

My co-pending U.S. Patent Application Ser. No. 011,160, filed Feb. 5, 1987, a disclosure of which is herein incorporated by reference, proposes various refinements and improvements to the two-part internal prosthesis. It proposes using a bone end pressure distributing means disposed completely within the residual limb and an open bottomed bone end containing means attached to the bone end pressure distributing means. The embodiments disclosed in the above-referenced application may be used with conventional external prosthesis, such as that disclosed in U.S. Pat. No. 2,578,019. Alternatively, by employing a bone pressure distributing means comprised of a magnetically attractive/transmissive material, the new and improved internal prosthesis disclosed in my co-pending application may be employed in conjunction with the device of the present invention.

None of the prior art external prostheses with which the inventor is acquainted have any provisions therein for inducing a massaging effort in the stump of the residual limb. One of the primary problems with amputees is poor circulation to the stump because the circulatory system has been disrupted. This problem is exacerbated by the convention external prostheses which even further inhibit the already poor circulation in the stump.

Thus, it would be desirable to provide an external prosthesis for use with an internal prosthesis attachable internally to a severed or amputated limb, said internal prothesis being comprised of a magnetically attractive/transmissive material. It would also be desirable to provide an external prosthesis which, when used in conjunction with the internal prosthesis disclosed in U.S. patent application Ser. No. 011,160, filed Feb. 5, 1987, would provide a more secure, non-slip fit, and enable the user to function in a comfortable and adaptive manner. It would also be desirable to provide an external prosthesis which is capable of massaging the residual limb to improve the internal circulation thereof.

SUMMARY OF THE INVENTION

The present invention is an external prothesis for use with a prothesis internally attachable to a residual limb having a bone with a free end thereof, said internal prothesis being comprised of a magnetically attractive/transmissive material. The external prosthesis of the instant invention comprises a synthetic body member of conventional shape and design having a concave socket formed at an end thereof. Said socket is sized to receive an internal prosthesis attached to a residual limb therein. The socket of the external prosthesis has an external surface which includes a magnetically attractive/transmissive layer disposed atop at least a portion of said external surface.

In one embodiment of the instant invention, the external prosthesis may further comprise a pressure deformable layer disposed adjacent the magnetically transmissive or receptive layer. Alternatively, the pressure deformable layer may also comprise the magnetically active layer. The pressure deformable layer may comprise a pressure conformable substance enclosed in coils. The pressure deformable substance may comprise a liquid gel.

The external prosthesis may further comprise means for switching the magnetic layer on and off to facilitate installation and removal of the external prosthesis from the residual limb. The switching means may be disposed within the external prosthesis or it may be disposed at a location on the user remote from the external prothesis.

Means may also be provided for causing a phase change in the liquid gel disposed within the pressure deformable layer. Rapid switching of either or both layers may be employed to cause a massage effect in the residual limb and promote the circulation thereof.

The magnetically transmissive/receptive layer may be disposed atop substantially the entire external surface of the socket. Alternatively, it may be disposed on only a portion of the external surface of the socket.

Because of the magnetic attraction between the magnet layer disposed in the socket of the external prosthesis and the magnet material of which portions of the internal prosthesis are comprised, a more secure and non-slip fit of the external prosthesis over the residual limb would be obtained. If the magnetic field is strong enough, this attraction alone will securely attach the limb to the stump. However, it may be desirable to employ straps, bands, or other devices known in the prior art as auxiliary fastening means. When used in conjunction with auxiliary fastening means in this manner, the invention described will permit a more comfortable and secure attachment. Also, the magnetic field may be used to stimulate motor response either of the external prosthesis, the internal prosthesis, the residual limb, or combinations thereof. By use of this invention, a greater degree of functioning and comfort will be permitted the user.

BRIEF DESCRIPTION OF THE DRAWINGS

The various features, advantages and uses of the present invention will become more apparent by reference to the following detailed description and drawings in which like reference numerals refer to multiple figures of the same structures throughout the drawings and in which.

DETAILED DESCRIPTION OF THE PREFERRED EMBODIMENTS

Figure 1:
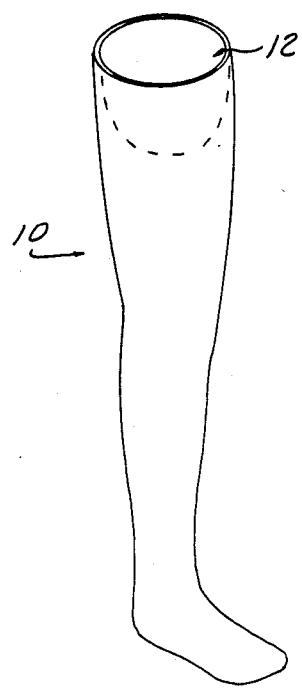
FIG. 1 is a perspective, partially cutaway view of an external prothesis of conventional design showing a socket disposed therein adapted to receive the stump of the residual limb.
Figure 2:
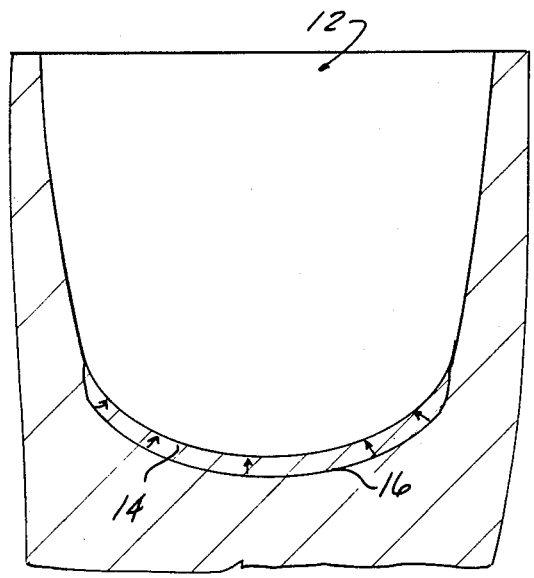
FIG. 2 is a perspective, partially cutaway view of one embodiment of the external prosthesis device of the present invention.

Referring now to FIGS. 1 and 2, there is illustrated an embodiment of the external prosthesis of the instant invention. FIG. 1 illustrates an artificial limb 10, in this case an artificial leg, of conventional design and fabricated of conventional materials. Formed at one end of the artificial limb 10 is a concave socket 12, the socket 12 being sized to receive the stump of a residual limb with an installed internal prosthesis (not shown) as described in my U.S. patent application Ser. No. 011,160, filed Feb. 5, 1987 attached thereto. As is conventional in the art, the size and shape of the socket 12 may be determined by casts of the artificial limb and internal prosthesis.

The concave socket 12 of the external prosthesis 10 has a concave external surface 14. Disposed atop at least a portion of the external surface 14 is a magnetically transmissive/receptive layer 16. The directions of the lines of force of the magnetic field are indicated by the arrows shown in FIG. 2. No particular polarity is indicated for the arrows because the invention will work equally well when the polarity is reversed, as long as the polarity is opposite that of the magnet material of the internal prosthesis.

It is contemplated that the magnetically transmissive/receptive layer 16 will be capable of being switched on and off. This switching ability will facilitate easy installation and removal of the external prosthesis 10, and, by rapidly switching the field on and off, a massaging effect will be induced which will help circulation to the stump. To this end, the magnetically transmissive/receptive layer 14 should be comprised of a soft magentic material, i.e. one characterized by a high initial permeability a small hysteresis curve, and a small coercive force Hc. Soft magnetic materials suitable for the purposes herein indicated might be, for example, a silicon-iron mesh, or a mesh impregnated with a silicon-iron. In order to induce a magnetic field in the soft magnetic material, an electromagnetic field is induced therein.

Figure 3:
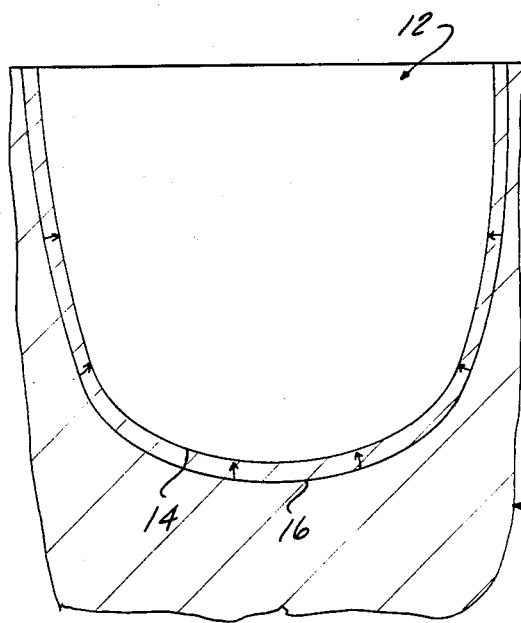
FIG. 3 is a perspective, partially cutaway view of an alternative embodiment of the internal prosthesis device of the instant invention.

In order to switch the magnetically transmissive/receptive layer 14 on and off, the device of the present invention may further comprise switching means 20 disposed within the external prosthesis. Switching means 20 is depicted schematically in FIG. 2. Alternatively, as shown in FIG. 3, switching means 20 may be elsewhere disposed on the body of the user or at a locational remote from the external prothesis 10. The switching means 20 may be connected via direct electrical connection to the magnetically transmissive/receptive layer 16, or it may emit a electromagnetic signal to perform the switching function.

In FIG. 2, the magnetically transmissive/receptive layer 16 is shown disposed on only a portion of the external surface 14 of concave socket 12. The embodiment shown in FIG. 2 would be particularly useful when used in conjunction with the embodiment of the internal prosthesis disclosed in may U.S. patent application Ser. No. 011,160, filed Feb. 5, 1987 shown in FIGS. 7 and 8 therein. Alternatively, as shown in FIG. 3 of the instant application, the magnetically transmissive layer 16 may be disposed over substantially entire external surface 14 of concave socket 12. The embodiment illustrated in FIG. 3 would find particular utility when used in conjunction of the embodiment of the internal prosthesis device disclosed in my U.S. patent application Ser. No. 011,160, filed Feb. 5, 1987 and illustrated in FIGS. 1-5 therein.

Figure 4:
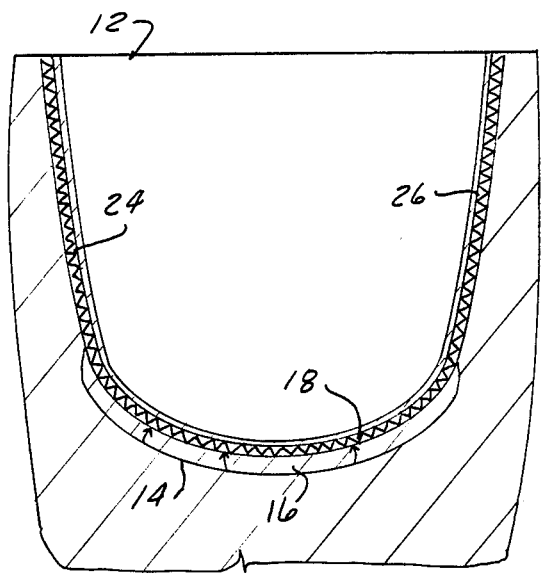
FIG. 4 is a perspective, partially cutaway view of an embodiment of the internal prosthesis device of the instant invention showing employment of a pressure deformable layer.
Figure 5:
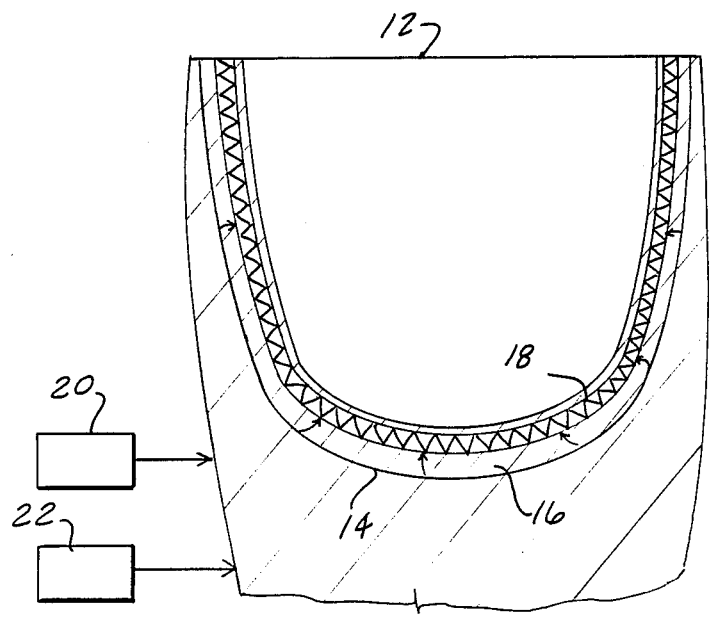
FIG. 5 is an alternative embodiment of the external prosthesis device shown in FIG. 4.

As shown in FIGS. 4 and 5 herein, the external prosthesis device 10 of the instant invention may further comprise a pressure deformable layer 18. FIGS. 4 and 5 show layer 18 disposed atop the magnetically transmissive/receptive layer 16, but layer 18 may also be disposed below layer 16 or a single layer may be formed as both magnetically active and pressure deformable. As shown in FIG. 4, if the magnetically transmissive/receptive layer 16 is disposed over only a portion of external surface 14, portions of pressure deformable layer 18 will be disposed directly atop those portions of external surface 14 uncovered by magnetically transmissive/receptive layer 16. FIG. 5 depicts magnetically transmissive/receptive layer 16 disposed over substantially over the entire surface 14, with pressure deformable layer 18 disposed atop magnetically transmissive/receptive layer 16.

The pressure deformable layer 18 may comprise a pressure conformable layer substance enclosed in coils. The pressure deformable substance may comprise a liquid gel. The purposed of pressure deformable layer 18 is to cushion the end of the residual limb to which external prosthesis 10 is attached, and helped to disperse and even out the pressure generated by the end of the bone of the residual limb pressing on the muscle and skin tissue thereof. It is also contemplated that use of pressure deformable layer 18 will help provide an even more secure and non-slip fit between external prosthesis 10 and the stump of the residual limb.

By utilizing a liquid/gel material as the pressure conformable substance, the phase change between the liquid and gel form of the material may be used to provide massage and stimulation to the stump of the residual limb in a manner analogous to switching the magnetic field on and off. To that end, control 22 is provided for switching of the material between its two phases. It is contemplated that control 22 could transmit radio, microwave, or other power frequency which would cause the liquid/gel to temporarily undergo a phase change. Alternatively, massage and stimulation may be provided by switching means 20 on and off. Thus breaking and re-establishing the magnetic attraction. Again, control 22 may be disposed within the residual limb or on the body of the user or at a remote location. Alternatively, pressure deformable layer 18 may also be formed without the gel. Alternating pressure caused by intermittently activating the magnetic field will enhance or stimulate circulation.

While the invention disclosed herein has been described with reference to certain illustrations and embodiments, it is not intended to be so limited but solely by the claims appended hereto.

I claim:

1. An external prosthesis comprised of a synthetic body member having a concave socket formed at an end thereof, said socket being sized to receive the stump of a residual limb with an internal prosthesis installed thereon, said external prosthesis having an external surface and a magnetically active layer disposed atop at least a portion of the external surface located at a stump receiving portion.

2. The prothesis of claim 1 further comprising a pressure deformable layer.

3. The prosthesis of claim 2 wherein the pressure deformable layer is disposed adjacent the magnetically active layer.

4. The prosthesis of claim 2 wherein the pressure deformable layer is magnetically active layer.

5. The prosthesis of claim 2 wherein the pressure deformable layer comprises a pressure deformable substance enclosed in coils.

6. The prosthesis of claim 5 wherein the pressure deformable substance comprises a liquid gel.

7. The prosthesis of claim 1 further comprising means for switching the magnetically active layer on and off.

8. The prosthesis of claim 7 wherein the switching means is disposed within the external prosthesis.

9. The prosthesis of claim 7 wherein the switching means is disposed at a location remote from the external prosthesis.

10. The prosthesis of claim 1 wherein the magnetically transmissive layer is disposed atop substantially the entire external surface of the socket.

11. The prosthesis of claim 2 further comprising means for switching the pressure deformable layer on and off.

12. The prosthesis of claim 11 wherein the switching means is disposed within the external prosthesis.

13. The prosthesis of claim 11 wherein the switching means is disposed at a location remote from the external prosthesis.

* * * * *